United States Patent [19]

Imperante et al.

[11] Patent Number: 5,280,099
[45] Date of Patent: Jan. 18, 1994

[54] SILICONE TAURINE POLYMERS

[75] Inventors: John Imperante, Lebanon, N.J.; Anthony J. O'Lenick, Jr., Lilburn, Ga.

[73] Assignees: Siltech Inc., Norcross, Ga.; Phoenix Chemical Co., Somerville, N.J.

[21] Appl. No.: 51,181

[22] Filed: Apr. 22, 1993

[51] Int. Cl.$^5$ ............................................. C08G 77/04
[52] U.S. Cl. .................................... 528/28; 556/425; 556/428
[58] Field of Search ................... 528/28; 556/425, 428

[56] References Cited

U.S. PATENT DOCUMENTS 5,073,619  12/1991  O'Lenick, Jr. .......................... 528/28
5,120,812   6/1992  O'Lenick, Jr. et al. ............... 528/28
5,166,297  11/1992  O'Lenick, Jr. .

Primary Examiner—Melvyn I. Marquis

[57] ABSTRACT

The present invention relates to a series of novel taurine functional silicone polymers, useful in softening hair, and fiber and conditioning skin.

Since the compounds of the present invention are high molecular weight silicone polymers, they have a high degree of oxidative stability, even at elevated temperatures.

The compounds of the present invention are prepared by the reaction of chloro silicone intermediate with a taurine derivative. In a preferred embodiment the hydroxy containing silicone polymer has been alkoxylated with ethylene oxide, propylene oxide or mixtures thereof. The ability regulate the type of alkylene oxide and amount present in the silicone polymer results in a series of products ranging in water/oil solubility. The technology used to produce the compounds of the present invention is very flexible and allows us to prepare performance tailored molecules for specific applications.

18 Claims, No Drawings

SILICONE TAURINE POLYMERS

BACKGROUND OF THE INVENTION

(1) Field of Invention

The present invention relates to a series of novel silicone derivatives ot taurine. These materials are surface active silicone compounds which are useful in a personal care and related applications.

Since the compounds of the present invention are high molecular weight silicone polymers, they have a high degree of oxidative stability, even at elevated temperatures. In addition, these compounds are non volatile and non irritating to eyes and skin.

The compounds of the present invention are prepared by the reaction of an intermediate prepared by the reaction of monochloroacetic acid with a pendant hydroxyl group which is present on a silicone polymer, resulting in chloro ester which in a subsequent step is reacted with taurine. In a preferred embodiment the hydroxy containing silicone polymer has been alkoxylated with ethylene oxide, propylene oxide or mixtures thereof. The ability regulate the type of alkylene oxide and amount present in the silicone polymer results in a series of products ranging in water/oil solubility.

(2) Object of the Invention

It is the object of the present invention to provide a series of novel silicone taurine polymers, which are substantive to skin and hair. This substantivity results in superior softening, conditioning and antistatic properties. The compounds contain varying amounts of ethylene oxide and propylene oxide in the molecule. This results in the ability to vary water solubility and introduce an inverse cloud point into the molecule. Inverse cloud point is well known to those skilled in the surfactant art. It is generally found in nonionic surface active agents. It is not found in quaternary compounds. The inverse cloud point is that temperature at which a soluble compound looses it's solubility in water. Inverse cloud point, also called high cloud point, is thought to be associated with the ability of the alkylene oxide chain to hydrogen bond with the water.

It is another objective of the current invention to provide silicone taurine derivatives which are nonirritating surface active agents. The compounds of the present invention have very low irritation values when applied to skin and eyes. Irritation is a major problem with traditional surfactants.

Application of the compounds of the invention can be from solvent, aqueous dispersion or solution, or applied neat in these process. It is anticipated that the effective conditioning concentration of the compound of this invention ranges from 0.1% to 25% by weight.

The silicone polymers, suitable as raw materials, in a preferred embodiment, contain varying amounts of ethylene oxide, propylene oxide or mixtures thereof. The presence of the oxide in the silicone polymer results in compounds with an inverse cloud point. Inverse cloud point phenomenon are well known to those skilled in the art of nonionic surface active agents. The inverse cloud point is defined as a temperature above which the polymer has minimal solubility in water. If heat is applied to an aqueous solution of the nonionic at the inverse cloud point the material will become insoluble, and the solution will turn milky. It is at this point that the polymer has minimal water solubility. Since the product is no longer in solution at the above this temperature, it is within this temperature range that the product has a maximum substantivity to a fiber. The ability to use temperature to deposit a lubricant, antistat onto a fiber offers a great advantage in cost effectiveness of fiber treatment, and results in less product usage.

(3) Description of the Arts and Practices

Silicone oils (polydimethylsiloxane) have been known to be active at the surface of plastic, cellulosic and synthetic fibers as well as paper. Despite the fact that they are lubricants that are stable to oxidation, their high cost and lack of durability has made them cost prohibitive in most application areas. Silicone oils need to be emulsified prior to application. This required high pressure equipment, surface active agents and generally results in a milky emulsion. Emulsions have experienced stability problems both in terms of freeze thaw instability and upon heating. This has resulted in minimal acceptance of them in commercial products.

The low efficiency of silicone oils is due to the fact that the oil is very water insoluble. Emulsions are generally prepared which contain silicone dispersed in micelles. While this method of application is easier for processing, much of the oil stays in the surfactant micelle and never gets deposited on the fiber. That which does deposit on the fiber surface remains there by hydrophobic binding, not ionic bonding. Since the polydimethylsiloxane is not bonded the effect is very transient. The product is removed with one washing.

Taurine derivatives are known to those skilled in the art. Taurine conforms to the following structure:

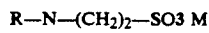

wherein R is alkyl, and M is a metal ion preferably an alkali metal such as sodium, potassium, ammonium or lithium.

The silicone chloro intermediate useful in the preparation of the compounds of the present invention are disclosed in U.S. Pat. No. 5,166,297 to O'Lenick, Jr. issued Nov. 24, 1992, which incorporated herein by reference.

None of the above incorporate silicone into compound. Consequently, the unique softening and substantivity properties achieved using the compounds of the present invention are not realized with the above technologies.

THE INVENTION

Summary of the Invention

The present invention relates to a series of novel silicone based taurine surfactants. These silicone polymers have a pendant taurine functional group present. The polymers by virtue of the pendent group deposit on hair, skin and fiber surfaces forming effective nonvolatile nonirritating, surface modifying finishes. The compounds of the present invention are excellent conditioners, antistats and non-yellowing, softeners.

The compounds of this invention are represented by the following formula;

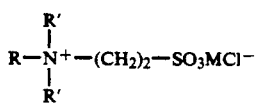

wherein
R is alkyl having from one to 40 carbon atoms;
R' is

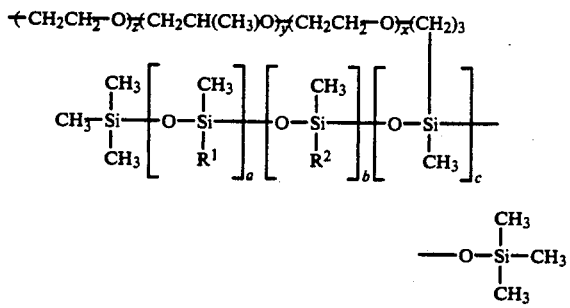

a is an integer from 0 to 200;
b is an integer from 0 to 200;
c is an integer from 1 to 200;
$R^1$ is selected from —$(CH_2)_n CH_3$ and phenyl;
n is an integer from 0 to 10;
$R^2$ is —$(CH_2)_3$—$(OCH_2CH_2)_x$—$(OCH_2CH(CH_3))_y$—$(OCH_2CH_2)_z$—OH;
x, y and z are integers and are independently selected from 0 to 20;
M is selected from the group consisting of Na, K, Li, and $NH_4$.

The products of the present invention are prepared by reaction of a halo containing silicone intermediate conforming to the following structure:

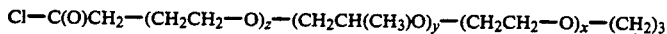

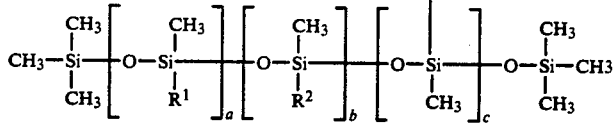

a is an integer from 0 to 200;
b is an integer from 0 to 200;
c is an integer from 1 to 200;
$R^1$ is selected from —$(CH_2)_n$—$CH_3$ and phenyl;
n is an integer from 0 to 10;
$R^2$ is —$(CH_2)_3$—$(OCH_2CH_2)_x$—$(OCH_2CH(CH_3))_y$—$(OCH_2CH_2)_z$—OH;
x, y and z are integers and are independently selected from 0 to 20;
with a taurine derivative conforming to the following structure:

R—N—$(CH_2)_2$—$SO_3$ M wherein R is alkyl having 1 to 40 carbon atoms, M is selected from the group consisting of Na, K, Li, and $NH_4$.

PREFERRED EMBODIMENTS

In a preferred embodiment x+y+z is zero.
In another preferred embodiment $R^1$ is methyl.
In still another preferred embodiment R is alkyl having 12–18 carbon atoms.
In another preferred embodiment M is Na.
In still another preferred embodiment M is K.
In a preferred embodiment x+y+z is greater than 0.
In a preferred embodiment b is zero.
In another preferred embodiment R is alkyl having 16 carbon atoms.

EXAMPLES (RAW MATERIALS)

One method of placing preparing the reactive hydroxyl containing silicone polymer is to react silanic hydrogen containing polymer with allyl alcohol or allyl alcohol alkoxylate monomer. Procedures this reaction are well known to those skilled in the art. U.S. Pat. No. 4,083,856 describe suitable processes.

Vinyl Intermediate Compounds

Compounds of this class are prepared by alkoxylation of allyl alcohol using methods well known to those skilled in the art. The following are some of the many compounds which can be used to make the products of this invention.

| $CH_2$=CH—$CH_2$—O—$(CH_2$—$CH_2$—O$)_x$—$(CH_2$—CH($CH_3$)—O$)_y$—$(CH_2$—$CH_2$—O$)_z$—H | | | |
|---|---|---|---|
| Designation | x | y | z | Molecular Weight |
| A | 3 | 0 | 0 | 189 |
| B | 9 | 27 | 3 | 2,178 |
| C | 11 | 3 | 0 | 718 |
| D | 0 | 0 | 0 | 57 |
| E | 20 | 20 | 20 | 2,940 |
| F | 20 | 0 | 0 | 880 |
| G | 10 | 10 | 10 | 1,470 |

Preparation of Intermediates

Silicone intermediates of the type used to make the compounds of this invention are well known to those skilled in the art. International Publication (Silicone Alkylene Oxide Copolymers As Foam Control Agents) WO 86/0541 by Paul Austin (Sep. 25, 1986) p.16 (examples 1 to 6) teaches how to make the following intermediates.

Hydrosilation of Intermediates
Silanic Hydrogen Containing Compounds

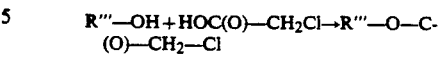

| Example | Austin Example | Group Designation | Average Molecular Weight | Equivalent Molecular Weight |
|---|---|---|---|---|
| 1 | 1 | MD 20 D' 3.2 M | 1,850 | 551 |
| 2 | 4 | MD 160 D' 5 M | 24,158 | 4,831 |
| 3 | 6 | MD 20 D' 10 M | 2,258 | 225 |

Hydrosilation Compounds

The hydrosilation reaction used to make the compounds of this invention are well known to those skilled in the art. One of many references is International Publication (Silicone Alkylene Oxide Copolymers As Foam Control Agents) WO 86/0541 by Paul Austin (Sep. 25, 1986) p. 19.

EXAMPLE 4

To a 22 liter three necked round bottom flask fitted with a mechanical agitator, thermometer with a Thermo-watch temperature regulator, nitrogen sparge tube vented reflux condenser and heating mantle is added 189.0 grams of Vinyl Intermediate Example #A. Next add 225 grams of Silanic Hydrogen Containing Compound Example #3 and 3,000 grams of toluene. Heat to 115° C. to remove azeotropically remove any water and 200 ml of toluene. The temperature is reduced to 85° C. and 3.5 ml of 3% H 2 PtCl 6 in ethanol is added. Light to then excluded from the flask by covering it with a black cloth. An exotherm is noted to about 95 C, while the contents are stirred for about 2 hours. During this time silanic hydrogen concentration drops to nil. Cool to 65 C and slowly add 60 g of sodium bicarbonate. allow to mix overnight and filter through a 4 micron pad. Distill off any toluene at 100 C and 1 torr.

EXAMPLE 5-10

The above procedure is repeated, only this time replacing both the silanic hydrogen compound #3 with the specified number of grams of the specified silanic hydrogen compound and the vinyl intermediate example A with the specified number of grams of the specified vinyl intermediate.

| Example | Vinyl Intermediate Example | Grams | Silanic Hydrogen Compound Example | Grams |
|---|---|---|---|---|
| 4 | A | 189.0 | 1 | 551.0 |
| 5 | B | 2,178.0 | 2 | 4,831.0 |
| 6 | C | 718.0 | 3 | 225.0 |
| 7 | D | 57.0 | 1 | 551.0 |
| 8 | E | 2,940.0 | 2 | 4,831.0 |
| 9 | F | 880.0 | 3 | 225.0 |
| 10 | G | 1,470.0 | 1 | 551.0 |

Preparation of the Ester Halide

Reaction Sequence $$R'''-OH + HOC(O)-CH_2Cl \rightarrow R'''-O-C(O)-CH_2-Cl$$

R''' contains the silicone portion of the molecule.

The following examples further illustrate the objects and advantages of this invention, though it should be understood that the various reactants and amounts thereof, reaction conditions, and other details are merely illustrative and should not be construed to unduly limit this invention.

General Procedure

Place the indicated amount of the dimethicone copolyol produced by the example shown in a suitable vessel. Add the desired amount of catalyst as shown under good agitation and a nitrogen sparge. The specified amount of monochloroacetic acid is added. A molar excess of 0.1 to 0.5 of monochloroacetic acid is added. The temperature is held between 180–225 degrees C. for four to six hours. Reaction progress is monitored by acid value analysis, which is a measure of free chloroacetic acid.

Suitable catalysts are esterification catalysts including, sulfuric acid, p-toluene sulfonic, methane sulfonic, tin metal, zinc metal, titanium metal, organotitinates, organotin compounds, organo zinc compounds, zinc oxide and other esterification catalysts. The preferred catalysts is stannous oxylate.

Chloroacetic acid is $Cl-CH_2-C(O)-OH$. It is also referred to as chloroethanoic acid, monochloroacetic acid, and MCA. It is an item of commerce.

Catalyst "A" below is stannous oxylate, Catalyst "B" is p-toluene sulfonic acid. Both are known esterification catalysts. Catalyst "B" was found to be more aggressive and result in a quicker reaction, however the color of the resulting product was darker. Catalyst "B" gave lighter colors but was somewhat slower. We found that using both the optimum catalyst system was attained.

| Example | Dimethicone Copolyol Example # | Grams | Grams of Chloro- Acetic Acid | Grams of Catalyst "A" | "B" |
|---|---|---|---|---|---|
| 11 | 4 | 740.0 | 100.0 | 0.4 | 0 |
| 12 | 5 | 7009.0 | 100.0 | 2 | 2 |
| 13 | 6 | 943.0 | 100.0 | 0 | 4 |
| 14 | 7 | 608.0 | 100.0 | 4 | 0 |
| 15 | 8 | 7771.0 | 100.0 | 2 | 2 |
| 16 | 9 | 1105.0 | 100.0 | 0 | 4 |
| 17 | 10 | 2021.0 | 100.0 | 4 | 0 |

Taurine Raw Materials

Alkyl taurine derivatives are commercially available from Nova Molecular Technologies.

These materials are prepared by the condensation of an amine with sodium isoethionate using an excess of the amine of about 6:1 to 2:1. The reaction is run at 230° C. for 6–24 hours removing water. The excess amine is distilled off under vacuum.

The reaction sequence is as follows:

HO—(CH₂)₂—SO₃M + R—NH₂ →
R—N—(CH₂)₂—SO₃M + H₂O ↑

| Example | Designation | R Group | M Group |
|---|---|---|---|
| 18 | Sodium N-methyl Taurine | CH3 | Na |
| 19 | Sodium N-butyl Taurine | C4H9 | Na |
| 20 | Potassium N-hexyl Taurine | C6H13 | K |
| 21 | Potassium N-lauryl Taurine | C12H25 | K |
| 22 | Sodium N-palmityl Taurine | C16H37 | Na |
| 23 | Potassium N-stearyl Taurine | C18H37 | K |
| 24 | Sodium N-octyl-dodecyl Taurine | C20H41 | Na |
| 25 | Sodium N-C40H81 Taurine | C40H81 | Na |

COMPOUNDS OF THE PRESENT INVENTION

It will be understood that the between one and two equivalents of silicone chloro intermediate to amine can be used depending upon the product desired.

General Reaction Procedure

The products of the present invention are generally prepared in aqueous solution or dispersion. The preferred concentration is about 50% solids. Additionally, alcohols such as methanol, ethanol, isopropanol, glycols such as ethylene glycol, propylene glycol, polypropylene glycol, polyethylene glycol, hexylene glycol, and cyclomethicone can be added to improve clarity if desired.

To a suitable flask, equipped with a thermometer and agitator is added the specified amount of water. Next add the specified amount of the type of silicone reactant. Heat to 50 C. Next add the specified amount of the specified taurine derivative under good agitation. The reaction mass is heated to 85–95 C. and held from between 5 and 15 hours. The reaction progress is monitored by % inorganic chloride, which approaches 98% of theoretical.

EXAMPLE 26

To a suitable flask, equipped with a thermometer and agitator is added 1,019.0 grams of water. Next add 834.0 grams of silicone reactant Example 11. Heat to 50 C. Next add 160.0 grams of taurine reactant Example 18 under good agitation. The reaction mass is heated to 85–95 C. and held from between 5 and 15 hours. The reaction progress is monitored by % inorganic chloride, which approaches 98% of theoretical.

The product is used as prepared without additional purification.

EXAMPLES 27–53

Example 26 is repeated only this time the specified amounts ant types of silicone reactant and taurine derivative is added replacing the taurine and silicone reactant used in example 26. The specified amount of water is added in place of the amount used in example 26.

| Example | Taurine Reactants Example | Grams | Silicone Reactants Example | Grams | Water Grams |
|---|---|---|---|---|---|
| 26 | 18 | 160.0 | 11 | 834.0 | 1,019.0 |
| 27 | 19 | 202.0 | 12 | 7,103.0 | 7,304.0 |
| 28 | 20 | 246.0 | 13 | 1,037.0 | 1,264.0 |
| 29 | 21 | 330.0 | 14 | 702.0 | 955.0 |
| 30 | 22 | 337.0 | 15 | 7,865.0 | 8,144.0 |
| 31 | 23 | 377.0 | 16 | 1,119.0 | 1,424.0 |
| 32 | 24 | 385.0 | 17 | 3,115.0 | 3,479.0 |
| 33 | 25 | 625.0 | 11 | 1,668.0 | 1,240.0 |
| 34 | 18 | 160.0 | 12 | 14,206.0 | 15,500.0 |
| 35 | 19 | 202.0 | 13 | 2,080.0 | 5,000.0 |
| 36 | 20 | 246.0 | 14 | 1,404.0 | 2,300.0 |
| 37 | 21 | 330.0 | 15 | 14,206.0 | 15,000.0 |
| 38 | 22 | 337.0 | 16 | 2,300.0 | 2,300.0 |
| 39 | 23 | 377.0 | 17 | 6,400.0 | 6,400.0 |
| 40 | 24 | 385.0 | 11 | 834.0 | 1,271.0 |
| 41 | 25 | 625.0 | 12 | 7,103.0 | 7,302.0 |
| 42 | 18 | 160.0 | 13 | 1,037.0 | 1,264.0 |
| 43 | 19 | 202.0 | 14 | 702.0 | 957.0 |
| 44 | 20 | 246.0 | 15 | 7,865.0 | 8,148.0 |
| 45 | 21 | 330.0 | 16 | 1,119.0 | 1,430.0 |
| 46 | 22 | 337.0 | 17 | 3,155.0 | 3,494.0 |
| 47 | 23 | 377.0 | 11 | 834.0 | 1,201.0 |
| 48 | 24 | 385.0 | 12 | 7,103.0 | 7,498.0 |
| 49 | 25 | 625.0 | 13 | 1,037.0 | 1,374.0 |
| 50 | 18 | 160.0 | 14 | 702.0 | 1,013.0 |
| 51 | 19 | 202.0 | 15 | 7,865.0 | 9,096.0 |
| 52 | 20 | 246.0 | 16 | 1,119.0 | 1,831.0 |
| 53 | 21 | 330.0 | 17 | 3,155.0 | 8,083.0 |

APPLICATIONS EXAMPLES

The compounds of the present invention are water soluble or dispersible and are substantive to hair and skin as well as being exceptionally well tolerated by skin. These properties of the compounds of the present invention make these compounds of major interest in personal care applications, specifically in soap bars were the lubricious feel of silicone combined with the detergency properties of the taurine derivative give very desirable skin feel.

What is claimed:

1. A silicone polymer which conforms to the following structure:

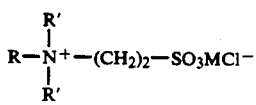

wherein:

R is alkyl having from 1 to 40 carbon atoms;
R' is

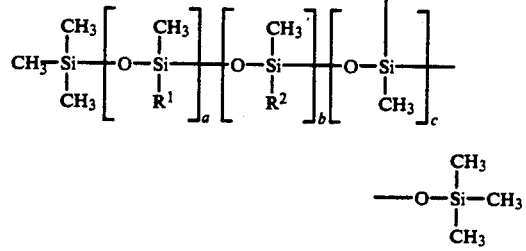

a is an integer from 0 to 200;
b is an integer from 0 to 200;
c is an integer from 1 to 200;
R¹ is selected from —(CH₂)ₙCH₃ or phenyl;

n is an integer from 0 to 10;

$R^2$ is —$(CH_2)_3$—$(OCH_2CH_2)_x$—$(OCH_2CH(CH_3))_y$—$(OCH_2CH_2)_z$—OH;

x, y and z are integers and are independently selected from 0 to 20;

M is selected from the group consisting of Na, K, Li, and $NH_4$.

2. A silicone polymer of claim 1 wherein x+y+z is zero.

3. A silicone polymer of claim 1 wherein $R^1$ is methyl.

4. A silicone polymer of claim 1 wherein R is alkyl having 12-18 carbon atoms.

5. A silicone polymer of claim 1 wherein M is Na.

6. A silicone polymer of claim 1 wherein M is K.

7. A silicone polymer of claim 1 wherein x+y+z is greater than 0.

8. A silicone polymer of claim 1 wherein b is zero.

9. A silicone polymer of claim 1 wherein R is alkyl having 16 carbon atoms.

10. A process for the preparation of a silicone polymer which comprises the reacting of a halo containing silicone intermediate conforming to the following structure:

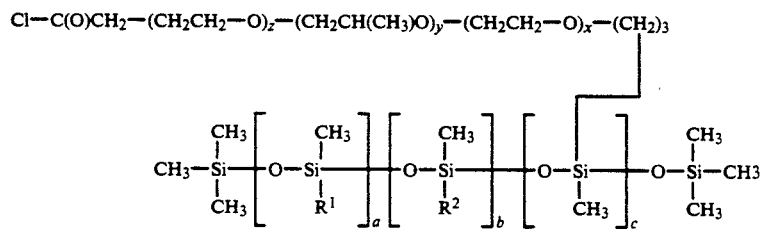

a is an integer from 0 to 200;
b is an integer from 0 to 200;
c is an integer from 1 to 200;
$R^1$ is selected from —$(CH_2)_n$—$CH_3$ or phenyl;

n is an integer from 0 to 10;

$R^2$ is —$(CH_2)_3$—$(OCH_2CH_2)_x$—$OCH_2CH(CH_3))_y$—$(OCH_2CH_2)_z$—OH;

x, y and z are integers and are independently selected from 0 to 20;

with a taurine derivative conforming to the following structure:

R—N—$(CH_2)_2$—$SO_3$ M wherein

R is alkyl having 1 to 40 carbon atoms,

M is selected from the group consisting of Na, K, Li, and $NH_4$.

11. A silicone polymer of claim 10 wherein x+y+z is zero.

12. A silicone polymer of claim 10 wherein $R^1$ is methyl.

13. A silicone polymer of claim 10 wherein R is alkyl having 12-18 carbon atoms.

14. A silicone polymer of claim 10 wherein M is Na.

15. A silicone polymer of claim 10 wherein M is K.

16. A silicone polymer of claim 10 wherein x+y+z is greater than 0.

17. A silicone polymer of claim 10 wherein b is zero.

18. A silicone polymer of claim 10 wherein R is alkyl having 16 carbon atoms.

* * * * *